United States Patent [19]

Klutchko et al.

[11] 3,989,714
[45] Nov. 2, 1976

[54] 3-PHENYLHYDROINDOLES

[75] Inventors: Sylvester Klutchko, Hackettstown, N.J.; Arch Christian Sonntag, Madison, Wis.; John Shavel, Jr., Mendham, N.J.

[73] Assignee: Warner-Lambert Company, Morris Plains, N.J.

[22] Filed: Oct. 21, 1974

[21] Appl. No.: 516,512

Related U.S. Application Data

[63] Continuation of Ser. No. 290,931, Sept. 21, 1972, abandoned.

[52] U.S. Cl. .................. 260/326.11 R; 260/590 C; 424/274; 424/331
[51] Int. Cl.[2] ....................................... C07D 209/04
[58] Field of Search........ 260/326.11, 319.1, 326.16

[56] References Cited
UNITED STATES PATENTS 3,028,394   4/1962   Popelak et al. .............. 260/319.1 X

*Primary Examiner*—Frederick E. Waddell
*Attorney, Agent, or Firm*—Albert H. Graddis; Frank S. Chow; George M. Yahwak

[57] ABSTRACT

The present invention discloses 3-phenylhydroindoles having the formula:

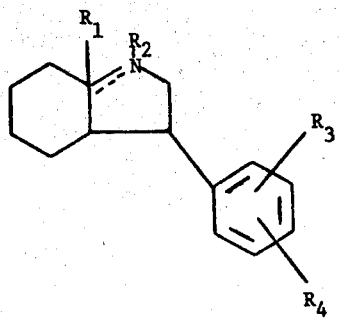

wherein $R_1$ may be hydrogen, lower alkyl, phenyl or may be absent; $R_2$ may be hydrogen, hydroxy, lower alkyl or absent; or where $R_1$ is absent $R_2$ may be $CH_3^+I^-$ or O; and $R_3$ and $R_4$ may be hydrogen, hydroxy or lower alkoxy. The compounds possess antiviral activity.

13 Claims, No Drawings

3-PHENYLHYDROINDOLES

This application is a continuation of application Ser. No. 290,931, filed 21 September 1972, now abandoned.

The present invention relates to certain phenylhydroindole compounds; and more particularly, the present invention relates to 3-phenylhydroindoles of the formula:

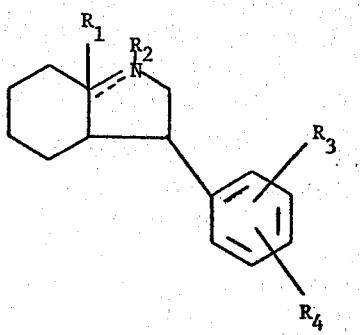

wherein $R_1$ may be hydrogen, lower alkyl, aryl or may be absent, $R_2$ may be hydrogen, hydroxy, lower alkyl or absent, or where $R_1$ is absent $R_2$ may be $CH_3{}^+I^-$ or O; $R_3$ and $R_4$ may be hydrogen, hydroxy or lower alkoxy.

The term lower alkyl as used herein includes hydrocarbons having 1 to 7 carbon atoms and includes straight chain as well as branched chain radicals. The term includes, for example, methyl, ethyl, propyl, isopropyl and the like. The term aryl as used throughout this disclosure denotes a monocyclic hydrocarbon radical preferably of 6 to 10 carbon atoms such as, for example, phenyl, tolyl and the like. Lower alkoxy as used herein is intended to include compounds having from 1 to 3 carbon atoms, for example, methoxy, ethoxy, propoxy and isopropoxy.

The production of the compounds of the present invention first requires the preparation of substituted β-nitrostyrenes. The preparation of these compounds is described in G. Tsalsas, Bull. Soc. Chim. France, 884–90 (1949). The nitrostyrenes useful in the present invention have the formula:

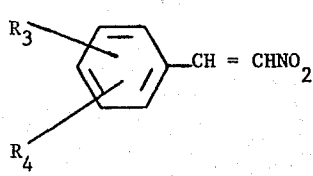

wherein $R_3$ and $R_4$ are as previously defined.

The above nitrostyrenes are reacted with the enamine from cyclohexanone and morpholine (Ref: Gilbert Stork, et al, J. Am. Chem. Soc. 85, 207 (1963) having the formula:

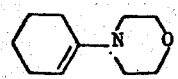

in an anhydrous neutral solvent, preferably dioxane, at room temperature for 1 – 24 hours to give the substituted cyclohexanone intermediates (Ref: M. Kuehne and L. Foley, J. Org. Chem. 30, 4280 (1965)), such as 2-[2-nitro-1-(3,4-dimethoxyphenethyl)] cyclohexanone, having the formula:

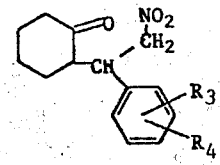

wherein $R_3$ and $R_4$ are as previously defined.

The preparation of novel nitrones of this invention, such as 3,3a,4,5,6,7-hexahydro-3-(3,4-dimethoxyphenyl)-2H-indoles 1-oxide, having the formula:

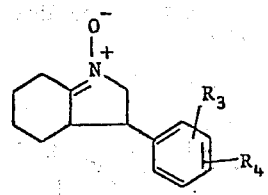

wherein $R_3$ and $R_4$ are as previously defined, involves a reduction of the above nitro compounds in an aqueous mixture of zinc dust and aqueous $NH_4Cl$ with an inert solvent at room temperature or slightly cooler.

The production of the novel compounds of this invention, such as 3-(3,4-dimethoxyphenyl)hexahydro-1-hydroxyindoline, having the formula:

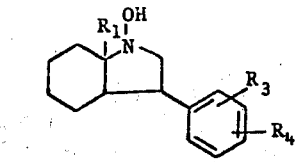

wherein $R_1$ = hydrogen and $R_3$ and $R_4$ are as previously defined, involves a potassium borohydride reduction of the above nitrones in a polar solvent, preferably water. Similar compounds, such as 3-(3,4-dimethoxyphenyl)-hexahydro-1-hydroxy-7a-methylindoline, having the above formula wherein $R_1$ = alkyl or aryl and $R_3$ and $R_4$ are as previously defined, may be prepared by reacting the intermediate nitrones with aryl or alkyl magnesium halides, such as methyl magnesium bromide, in an aprotic solvent such as tetrahydrofuran.

The above N-hydroxy compounds can be transformed into further novel compounds by reducing with zinc and dilute hydrochloric acid, preferably 1-Normal concentration, at elevated temperatures, preferably 100° C, to give compounds having the formula:

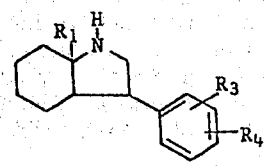

wherein $R_1$ = hydrogen, alkyl or aryl; $R_3$ and $R_4$ are as previously defined.

The above secondary amines can be transformed into further novel compounds of this invention, such as 3-(3,4-dimethoxyphenyl)hexahydro-1,7a-dimethylindoline, having the formula:

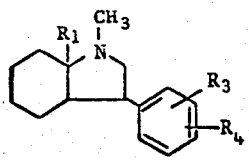

wherein $R_1$ = alkyl or aryl and $R_3$ and $R_4$ are as previously defined, by use of the Eschweiler-Clarke methylation conditions with formaldehyde and formic acid.

The above nitrones may be deoxygenated with zinc and dilute hydrochloric acid at 100° C to give further novel compounds of this invention, such as 3-(3,4-dimethoxyphenyl-3,3a,4,5,6,7-hexahydro-2H-indole, having the formula:

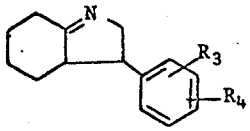

wherein $R_3$ and $R_4$ are as previously defined.

The following examples are included to further illustrate the invention.

EXAMPLE 1

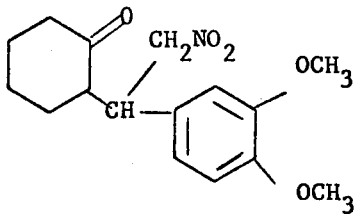

2-[2-Nitro-1-(3,4-dimethoxyphenethyl)]cyclohexanone

A quantity of 16.7 g (0.1 mole) of morpholinocyclohexene is added to a stirred mixture of 19.0 (0.09 mole) of 3,4-dimethoxy-$\beta$-nitrostyrene and 200 ml of dioxane at room temperature. Gradually (15 min.) all solid goes into solution and the solution is allowed to stand overnight. Dilute hydrochloric acid (100 ml of 3N) is added and the solution is warmed on the steam bath for 5 minutes. Water (500 ml) is added and the yellow viscous material which separates crystallizes. After filtration and water wash the solid is dried and weighed to give 24.7 g (89.2%) of product melting at 140°–142° C. Recrystallization from 600 ml of 2-propanol gives 20.3 g of pale yellow crystals melting at 141°–143° C.

Anal. Calcd for $C_{16}H_{21}NO_5$: $C_1$, 62.52; H, 6.88; N, 4.56. Found: C, 62.72; H, 7.06; N, 4.35.

EXAMPLE 2

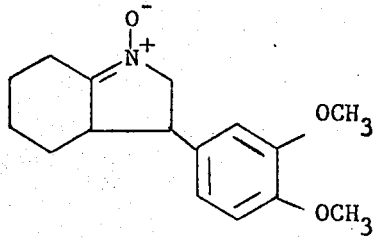

3,3a,4,5,6,7-Hexahydro-3-(3,4-dimethoxyphenyl)-2H-indole 1-oxide

To a solution of 19.0 g (0.062 mole) of 2-[2-nitro-1(3,4-dimethoxyphenethyl)]cyclohexanone in 180 ml of tetrahydrofuran was added 60 ml of water and 3 g (0.006 mole) of ammonium chloride. With stirring and ice bath cooling, 23.0 g of zinc dust was added over a period of ½ hour, keeping the temperature at ca 10° C. After another ½ hour stirring in the ice bath and then 1½ hours stirring at room temperature, the inorganics were filtered and washed with 100 ml of methanol. Most of the THF and methanol was removed on the rotary vacuum evaporation and 200 ml of 1N hydrochloric acid was added. Some insoluble neutral material was filtered off and solid potassium carbonate was added to neutralize the acid and then enough was added to completely saturate the solution. The viscous product was extracted into 400 ml of methylene chloride (top layer) and the extract was dried ($K_2CO_3$), filtered, and concentrated. The viscous residue was dissolved in 75 ml of warm ethyl acetate and 75 ml of petroleum ether was added. On seeding white crystals separated; wt. 11.5 g (67.7%), mp 135°–141° C. Recrystallization was effected most satisfactorily by dissolving in 50 ml of hot methylene chloride, adding 100 ml of ethyl acetate, concentrating to ca 75 ml volume (at atmospheric pressure) and cooling. Pure white crystals (7.5 g) were obtained; mp 142°–143° C.

Anal. Calcd for $C_{16}H_{21}NO_3$: C, 69.79; H, 7.69; N, 5.09. Found: C, 69.66; H, 7.69; N, 5.34.

EXAMPLE 3

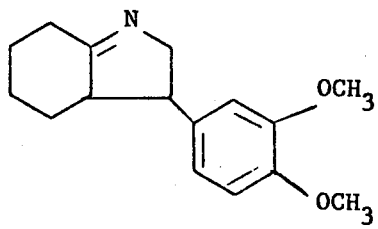

3-(3,4-Dimethoxyphenyl)-3,3a,4,5,6,7-hexahydro-2H-indole hydrochloride

A solution of 9.0 g (0.033 mole) of 3,3a,4,5,6,7-hexahydro-3-(3,4-dimethoxyphenyl)-2H-indole 1-oxide in 100 ml of 1N hydrochloric acid and 50 ml of water was heated with stirring with 19.5 g (0.3 mole) of zinc dust on the hot plate to ca. 100° for 15 minutes. The mixture was cooled and ca. 100 ml of 10M potassium hydroxide and 400 ml of ether were added. The mixture was stirred vigorously and then filtered through glass wool. The aqueous phase was separated and the ether phase was dried ($K_2CO_3$), filtered and concentrated to give 5.4 g (63.2%) of a tacky solid. This material was triturated with 10 ml of ether and filtered to give 3.3 g of low melting base. This material was dissolved in 50 ml of ethyl acetate and hydrogen chloride gas was added to precipitate the crystalline salt, wt 3.6 g, mp 230°–233°. Recrystallization from methanol-ether afforded pure hydrochloride melting at 231°–234° C.

Anal. Calcd for $C_{16}H_{21}NO_2 \cdot HCl$: C, 64.97; H, 7.50; N, 4.74. Found: C, 64.71; H, 7.56; N, 4.49.

EXAMPLE 4

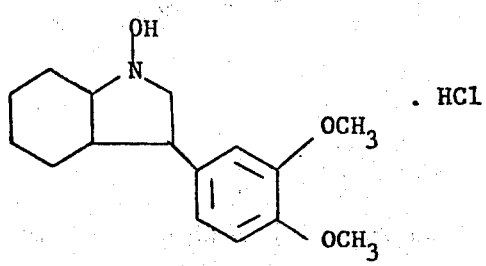

3-(3,4-dimethoxyphenyl)hexahydro-1-hydroxyindoline hydrochloride

A solution of 8.0 g (0.029 mole) of 3,3a,4,5,6,7-hexahydro-3-(3,4-dimethoxyphenyl)-2H-indole 1oxide in 75 ml of methanol was treated with stirring with 1.9 g (0.05 mole) of sodium borohydride. The mixture became warm and there was some foaming. It was cooled to room temperature and stirred for 1½ hours. Water (200 ml) was added and the separated material was extracted into 400 ml of ether. The ether solution was washed with two 100 ml portions of water, dried ($K_2CO_3$) and treated with hydrogen chloride gas to precipitate a tacky salt. The turbid supernatant was decanted and the residue dissolved in 100 ml hot 2-propanol. With addition of 500 ml of ether white crystals slowly separated; wt. 5.6 g (61.8%), mp. 175°–179° C. Recrystallization from methanol-ether afforded pure white crystals melting at 177°–181° C.

Anal. Calcd for $C_{16}H_{21}NO_3 \cdot HCl$: C, 61.24; H, 7.71; N, 4.46 Found: C, 61.31; H, 7.87; N, 4.30.

EXAMPLE 5

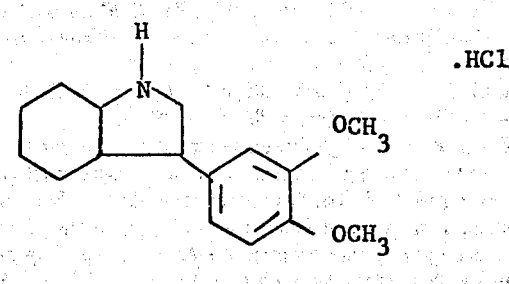

3-(3,4-Dimethoxyphenyl)hexahydroindoline hydrochloride

A mixture of 10.0 g (0.036 mole) of 3-(3,4-dimethoxyphenyl)hexahydro-1-hydroxyindoline base, 400 ml of 1N hydrochloride acid (0.4 mole) and 20 g of zinc dust was heated with stirring on the steam bath for 1½ hours. The cooled mixture was decanted (still acid to congo red) and 10M KOH (150 ml) was added. The separated oil was ether extracted (800 ml) and the ether solution was dried ($K_2CO_3$), filtered and treated with HCl gas to precipitate solid salt; wt. 9.5 g (84.2%), mp 188°–198° C. Recrystallization from 2-propanol-ether gave pure material melting at 190°–192° C.

Anal. Calcd for $C_{16}H_{23}NO_2 \cdot HCl$: C, 64.53; H, 8.12; $Cl^-$, 11.90. Found: C, 64.53; H, 8.15; $Cl^-$, 12.02.

EXAMPLE 6

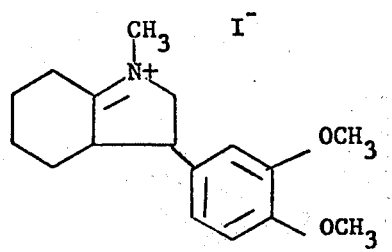

3-(3,4-dimethoxyphenyl)-3,3a,4,5,6,7-hexahydro-1-methyl-2H-indolinium iodide

A quantity of 8.0 g (0.031 mole) of 3-(3,4-dimethoxyphenyl)-3,3a,4,5,6,7-hexahydro-2H-indole base was added to 60 ml of methyl iodide. All solid dissolved as the solution became hot and refluxed vigorously as the solid quaternary separated. After ten minutes the mixture was concentrated to ca ½ volume. Ether (100 ml) was added and the product was filtered and washed with ether, wt. 12.3 g (quantitative yield), mp. 185°–187° C. Recrystallization from methanol gave pure, pale yellow crystals melting at 189°–191° C.

Anal. Calcd. for $C_{16}H_{21}NO_2 \cdot CH_3I$: C, 50.88; H, 6.03; N, 3.49. Found: C, 50.59; H, 6.31; N, 3.47.

EXAMPLE 7

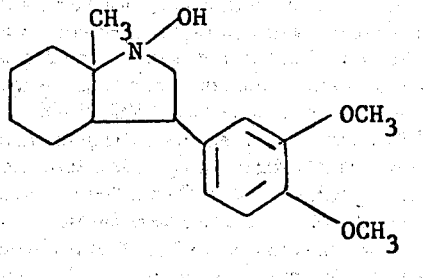

3-(3,4-Dimethoxyphenyl)hexahydro-1-hydroxy-7a-methyl-indoline

A volume of 10 ml of 3M methyl magnesium bromide in ether was added over a period of two minutes to a stirred solution of 4.12 g (0.015 mole) of 3,3a,4,5,6,7-hexahydro-3-(3,4-dimethoxyphenyl)-2H-indole 1-oxide in 25 ml of tetrahydrofuran. The warm solution was stirred for ½ hour at room temperature and then added cautiously to 50 ml of ice water. The mixture was stirred for 5 minutes and solid potassium carbonate was added to saturate. The mixture was extracted into 200 ml of ether and the extract was decanted, dried over $K_2CO_3$, filtered and concentrated to ca 50 ml volume. The separated crystals were filtered and washed with ether; wt. 2.5 g, mp 147°–149° C. A second crop weighing 0.6 g was obtained for a total weight of 3.1 g (71% yield). The product was recrystallized from ethyl acetate to give pure white crystals melting at 147°–149° C.

Anal. Calcd for $C_{17}H_{25}NO_3$: C, 70.07; H, 8.65; N, 4.81. Found: C, 70.17; H, 8.65; N, 4.97.

EXAMPLE 8

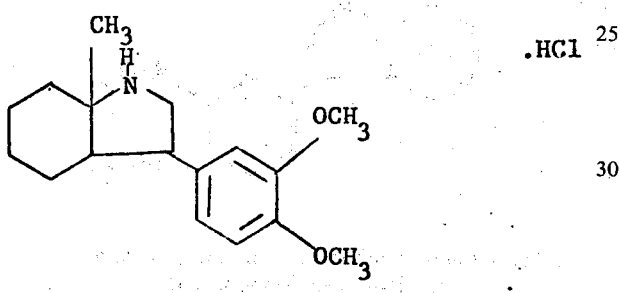

3-(3,4-dimethoxyphenyl)hexahydro-7a-methylindoline hydrochloride

A mixture of 35.0 g (0.12 mole) of 3-(3,4-dimethoxy-phenyl)-hexahydro-1-hydroxy-7a-methylindoline, 800 ml of 1N hydrochloric acid, 600 ml of methanol and 45.8 g (0.7 mole) zinc dust was heated with stirring to the boiling point in an apparatus set up for distillation. The methanol was allowed to slowly distill over 1½ hours. After cooling the pH of the mixture was still acid (ph < 2). The supernatant was decanted from unreacted zinc and the zinc was washed with 200 ml of water and this was decanted. With cooling, the combined decantates were treated 10M potassium hydroxide until strongly basic (to dissolve zinc salts). Solid potassium carbonate was then added to saturate the solution. The oily base was extracted into 1-1 of ether; the solution was dried over $K_2CO_3$ and filtered.

The hydrochloride salt was prepared by passing hydrogen chloride gas into the above ether solution until complete precipitation of white solid, wt 39.7 g, mp 201°–203°. Theory is 37.4 g. This material was apparently damp. Recrystallization from methanol-ether gave 25.8 g (68.9%) of pure white crystals melting at 202°–204°.

Anal. Calcd for $C_{17}H_{25}NO_2.HCl$: C, 65.48; H, 8.40; N, 4.49. Found: C, 65.42; H, 8.47; N, 4.49.

EXAMPLE 9

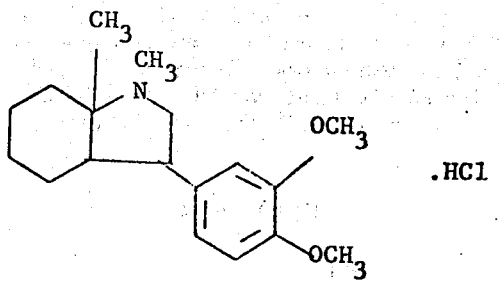

3-(3,4-dimethoxyphenyl)hexahydro-1,7a-dimethylindoline

A mixture of 14.5 g (0.053 mole) of 3-(3,4-dimethoxyphenyl)hexahydro-7a-methylindoline base and 9.73 g (0.12 mole) of 37% formaldehyde was warmed on the steam bath for 5 minutes, 400 ml glacial acetic acid was added, and the solution was heated at 100° C for 8 hours and then refluxed for 3 hours. Most of the acetic acid was stripped off. Water (100 ml) was added, and the solution was made basic with 10 M potassium hydroxide. The separated oil was extracted into 800 ml of ether; the solution was dried ($K_2CO_3$), filtered, and concentrated to give a viscous oil. Purification: To remove any unreacted starting material (secondary amine), an acetylation was run by refluxing the oil with 25 ml of acetic anhydride. Water (500 ml) was added, and the mixture was stirred for 5 minutes. Charcoal and "Super Cel" were added to remove turbidity (N-acetyl derivative of starting material). The filtered solution was basified with 10 M potassium hydroxide and the separate oil was extracted into 600 ml of ether. The solution was dried over potassium carbonate and filtered. Preparation of hydrochloride salt: The above ether solution was treated with excess hydrogen chloride gas to precipitate a pale yellow tacky salt. This was dissolved in 50 ml of hot absolute ethanol. Ether (ca.500 ml) was added to precipitate crystals, wt. 7.5 g (43.6%), mp 234°–236° C. Recrystallization from ethanol-ether gave pure, pale yellow crystals melting at 234°–236° C.

Anal. Calcd for $C_{18}H_{27}NO_2.HCl$: C, 66.34; H, 8.66; N, 4.30. Found: C, 66.29; H, 8.73; N, 4.06

This compound, by elemental analysis and nmr, is the N-methyl derivative. The Eschweiler-Clarke methylation was effected. The formic acid needed in this reaction apparently arose from air oxidation of the excess formaldehyde in the reaction medium. There is precedent for N-methylation with only formaldehyde. See Organic Reactions 5, Chapt. 7, p. 307.

EXAMPLE 10

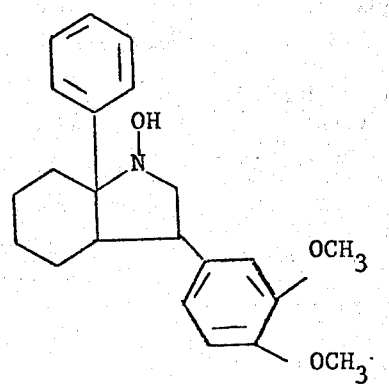

3-(3,4-dimethoxyphenyl)hexahydro-1-hydroxy-7a-phenylindoline

A volume of 75 ml of 3 M phenylmagnesium bromide in ether was added over a period of five minutes to a warm (35° C) stirred solution of 41.25 g (0.015 mole) of 3,3a,4,5,6,7-hexahydro-3-(3,4-dimethoxyphenyl)-2H-indole-1-oxide in 500 ml of tetrahydrofuran. After stirring for 2 hours at room temperature, most of the THF was distilled off at atmospheric pressure. Ice water (1 liter) was added and the paste-like solid was filtered. The damp filter cake was added to 500 ml of 1N HCl. The taffy-like material which remained out of solution was added to 10 MKOH (300 ml). The mixture was extracted into 1.5 l methylenechloride and the extract was dried ($K_2CO_3$), charcoaled, filtered and concentrated. The residue was dissolved in 200 ml of petroleum ether. There was obtained 12.5 g (23.6%) of a white solid melting at 166°–168° C. Recrystallization from 2-propanol gave pure material melting at 168°–170° C.

Anal. Calcd for $C_{22}H_{27}NO_3$: C, 74.75; H, 7.70; N, 3.96. Found: C, 74.78; H, 7.67; N, 3.77.

EXAMPLE 11

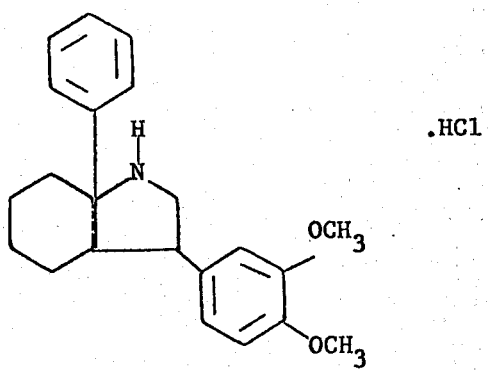

3-(3,4-dimethoxyphenyl)hexahydro-7a-phenylindoline hydrochloride

Zinc powder (20 g) was added to a stirred solution of 6.5 g (0.018 mole) of 3-(3,4-dimethoxyphenyl)-hexahydro-1-hydroxy-7a-phenylindoline, 150 ml of methanol and 150 ml of 1N hydrochloric acid and the mixture was maintained at reflux for ½ hour. The mixture was cooled, treated with excess of 10MKOH and extracted with two one liter portions of ether. The extracts were combined, dried ($K_2CO_3$) and filtered. Hydrogen chloride gas was bubbled into the ether solution until complete precipitation of the white salt; wt. 4.5 g (67.2%), mp 303°–305° C. Recrystallization from methanol-ether afforded pure white crystals, mp 303°–305° C.

Anal. Calcd for $C_{22}H_{27}NO_2 \cdot HCl$; C, 70.67; H, 7.55; N, 3.75 Found: C, 70.87; H, 7.67; N, 3.59.

EXAMPLE 12

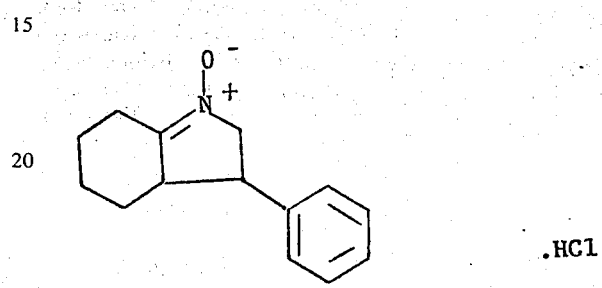

3,3a,4,5,6,7-Hexahydro-3-phenyl-2H-indole 1-oxide hydrochloride

A solution of 3.0 g ammonium chloride in 60 ml of water was added to a solution of 15.0 g (0.06 mole) of 2-(2-nitro-1-phenethyl)cyclohexanone in 180 ml of tetrahydrofuran. Zinc dust (23 g) was added portionwise with stirring at 5°–10° C over a period of 1 hour. After stirring an additional hour at room temperature the mixture was filtered and the filter cake was washed with 50 ml of methanol. The filtrate was concentrated to remove most of the methanol and THF and 200 ml of 1N hydrochloric acid was added. A small amount of insoluble material was extracted away into 500 ml of ether. The aqueous layer was separated, neutralized with potassium carbonate, saturated then with solid potassium carbonate and extracted with 500 ml of methylene chloride. The organic solution was dried over $K_2CO_3$, filtered and concentrated to give a colorless viscous material.

The hydrochloride salt was prepared by dissolving the crude base in 200 ml of ethyl acetate and passing-in hydrogen chloride to precipitate crystalline salt. Ether (200 ml) was added and the solid filtered; wt 10.0 g (66.6% yield), mp 105–108. This pink solid was recrystallized from methanol-ether to give pure material melting at 108°–110° C.

Anal. Calcd for $C_{14}H_{17}NO \cdot HCl$: C, 66.79; H, 7.21; N, 5.56. Found: C, 66.86; H, 7.22; N, 5.60.

EXAMPLE 13

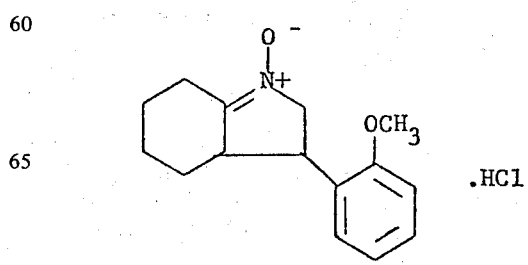

3,3a,4,5,6,7-hexahydro-3-(o-methoxyphenyl)-2H-indole 1-oxide hydrochloride

Water (60 ml) and ammonium chloride (3.0 g) were added to a solution of 19.0 g (0.068 mole) of 2-[2-nitro-1-(0-methoxyphenethyl)] cyclohexanone in 180 ml of tetrahydrofuran. The solution was cooled to 5°–10° in an ice bath and with vigorous stirring, 23.4 g of zinc powder was added over a one hour period. The mixture was removed from the ice bath and stirred for 1½ hours at room temperature. The zinc was filtered off and the filtrate was stripped of T.H.F., treated with 200 ml of 1NHCl, extracted with 300 ml of ether to remove traces of neutral material, neutralized and then saturated with solid potassium carbonate. The separated oil was extracted into 400 ml of methylene chloride; the solution was dried ($K_2CO_3$), filtered and concentrated. The oily base was dissolved in 300 ml of ethyl acetate and treated with a slight excess of hydrogen chloride. Ether (200 ml) was added and the pink solid was filtered and washed with ether, wt. 15.5 g (80.8% Yield), mp 120°–122° C. Recrystallization from methanol-ether, gave pure faint pink crystals melting at 123°–124° C.

Anal. Calcd. for $C_{15}H_{19}NO_2 \cdot HCl$: C, 63.94; H, 7.15; N, 4.97. Found: C, 64.06; H, 7.23; N, 4.71.

Compounds of the present invention show antiviral activity in concentrations of 50 to 100 γ/ml when tested in liquid media using the procedure of Rightsel (Univ. of Mich. Med. Bull. 24:222–234 (1958)) and on solid media using the Herrmann modification of the Dulbecco Technique (Proc. Nat. Acad. Sci., Wash. 38:747–752 (1952); Proc. Soc. Exp. Bio., N.Y., 103: 625–628 (1960)).

More particularly the protocol for the Rightsel procedure used is as follows:

| | ANTIVIRAL ACTIVITY TUBE METHOD |
|---|---|
| PURPOSE: | The determination of toxicity and antiviral activity of experimental compounds in normal and cancer cell lines in vitro in tubes with liquid culture media. |
| MATERIALS: | Cell Lines - cancer<br>HeLa - Human Carcinoma of the Cervix<br>Virus - Rhinovirus 2 (HGP)<br>Growth Medium - Basal Medium Eagle (BME) with Earle's salts, containing 10 % fetal bovine serum, penicillin (100 units/ml.) and streptomycin (100 mcg./ml.)<br>Maintenance Medium - A 1:1 mixture of BME and Medium 199; contains 2 % fetal bovine serum.<br>Trypsin - (1–300) 0.25 % in Ca-free and Mg-free Hanks' balanced salt solution (BSS)<br>Roller Bottles - Bellco<br>Tubes - Sterile 16 × 150 mm plastic screw top tubes.<br>Roller bottles are seeded with approximately $10^7$ cells in 250–300 of growth medium and rotated at 0.5 rpm on the Bellco roller apparatus at 37° C until the cell sheet is confluent.<br>Trypsinization - Cells are resuspended in growth medium at a concentration of 2.25 × 10⁰ HeLa cells/ml. The cell suspensions are gassed with $CO_2$ to a pH of 6.8. Sterile plastic tubes are seeded with 1.0 ml of cell suspension and incubated in a stationary position for two days (until cell sheet is confluent). |
| COMPOUND PREPARATION: | The compound is dissolved in distilled water at a maximum concentration of 500 gamma/ml. Where necessary, NaOH, HCl or ethanol is used to dissolve the material. The pH of the final solution is adjusted as closely as possible to pH 7.2. This stock solution is then diluted with medium to contain appropriate concentrations of the compound. |
| VIRUS PREPARATION: | The virus is thawed rapidly at 37° C and diluted 10-fold in maintenance medium - to $10^{-8}$ for titration and to an estimated 10 – 100 Tissue Culture Infectious Dose₅₀ ($TCID_{50}$) for test. |
| TEST PROCEDURE: | The growth medium is decanted from the cell sheet in the plastic tubes.<br>Adsorbed virus system: 0.1 ml of virus dilution is added to each of the tubes and the tubes are rolled at 33° C for 1 hour. Cytotoxicity and control tubes are rolled with just 0.1 ml of medium. After a 1 hour adsorption period, 0.9 ml of the appropriate dilution of the test compound is added to each of the tubes and the tubes are returned to the roller apparatus.<br>Unadsorbed virus system: 0.1 ml of the diluted virus and 0.9 ml of the diluted test compound are added simultaneously to a tube and the tubes rotated at 33° C. |
| RECORDING: | HeLa cell cultures are read every day, starting on day 3 and readings are continued until culture controls have shown a non-specific cytopathic effect (CPE) in about 5–6 days. WI-38 cultures are read every other day, starting with day 3, for 10–14 days.<br>Compound cytoxicity is recorded as 0 – 4+, depending on the degree and nature of the CPE. Viral CPE is also recorded as 0 – 4+, depending on the percent of the cell sheet showing virus growth. Four tubes are used for each concentration of compound and for each concentration of virus dilution, and the four CPE ratings within each group are averaged.<br>To be considered active, a specific concentration of a test |

ANTIVIRAL ACTIVITY TUBE METHOD compound must average 2 or more points below that of the virus control. Actual $TCID_{50}$ of virus used is calculated by method of Reed and Muench.

The procedure for the Herrmann modification used is as follows:

| | |
|---|---|
| TEST NAME: | Antiviral Activity, Solid Media |
| PURPOSE: | The determination of toxicity and antiviral activity of experimental compounds in normal and cancer cell lines as measured by plaque suppression in solid media. |
| MATERIALS: | Cell Line - Cancer<br>HeLa - Human carcinoma of the cervix<br>Virus - Rhinovirus 2 (HGP)<br>Growth Medium - Basal Medium Eagle (BME) containing 10 % fetal bovine serum, penicillin (100 units/ml) and streptomycin (100 mcg/ml).<br>Trypsin - (1-300) 0.25 % trypsin in Ca-free and Mg-free Hanks' balanced salt solution (BSS).<br>Maintenance Medium-<br>(1) Rhinovirus: A 1:1 mixture of BME and Medium 199. Contains 2 % fetal bovine serum (FBS); 30 mM $MgCl_2$; 0.3 % Tris; 30 gamma/ml diethylaminoethyl (DEAE) dextran and 1 % Bacto-Agar (Difco);<br>Wash Fluid - Phosphate-buffered saline (PBS) containing 0.4 % bovine albumin.<br>Discs - Sterile Schleicher and Schuell ¼" penicillin assay discs.<br>Plates - Falcon plastic 60 × 15 mm dishes.<br>Roller Bottles - Bellco |
| CELL PREPARATION: | Roller bottles are seeded with approximately $10^7$ cells in 250-300 ml of growth medium and rotated at 0.5 rpm on the Bellco roller apparatus at 37° C until the cell sheet is confluent.<br>Cells are removed from the glass surface with trypsin. The cells are resuspended in medium to a concentration of $2.0 \times 10^5$/ml. Falcon plastic 60 × 15 mm plates are seeded with 5.0 ml of cell suspension and incubated for 48 hours at 37° C in Pyrex baking dishes sealed with Saran-wrap. Before each baking dish is sealed sufficient $CO_2$ is introduced into the atmosphere to maintain a media pH of from 7.2 – 7.4. |
| DISC PREPARATION: | Water-soluble compounds are prepared in distilled water with the aid of HCl or NaOH as necessary. Solutions are Millipore filtered. Water insoluble compounds are solubilized.<br>Sterile Schleicher and Schuell ¼" penicillin assay discs are soaked in compound solutions for one hour in a closed container at room temperature and then dried at 37° C in glass 60 × 15 mm petri dishes. |
| TEST PROCEDURE: | Media are removed from plates by suction and the cell layer is washed with phosphate-buffered saline (PBS) containing 0.4 % bovine albumin.<br>Dilutions of stock virus of $10^{-1}$ through $10^{-8}$ are made in maintenance medium (without agar). Based on previous titrations, 1.0 ml of one of the above viral suspensions estimated to contain approximately 200 plaque forming units (PFU) for Rhinovirus is added to each test plate. In parallel with the test, 1.0 ml of the above viral suspensions is also plated in order to titrate the virus and determine the exact number of PFU used in the test. Control and cytotoxicity plates each receive 1.0 ml media. All plates are incubated for 2 hours at room temperature sealed in Pyrex baking dishes on the Bellco rocker platform. After the adsorption period the virus inoculum is removed and the plates are washed again with PBS to remove unadsorbed virus. Each plate is now overlayed with 9.0 ml of maintenance media.<br>When the agar is sufficiently hardened, previously prepared discs are placed in the center of each plate. The plates are again sealed in $CO_2$-gassed baking dishes and incubated at 33° C for Rhinovirus. |
| RECORDING: | After 4 days incubation, the plates are overlayed with 5.0 ml of 0.15 % 2-(p-iodophenyl)-3-(p-nitrophenyl)-5-phenyl tetrazolium chloride (INT) in 1 % Bacto-Agar and incubated 6–18 hours at 37° C. Zones of cytotoxicity (unstained) and antiviral activity (plaque-free) are measured across the entire diameter (including disc). The number of plaques on titration plates are counted to |

-continued

| | | Cell | | Virus | | Activity | |
|---|---|---|---|---|---|---|---|
| Compound | Protocol | Line | Virus | Concentration | Cytotoxicity | | Antiviral |
| Example 13 | Tube | HeLa | Rhinovirus 2 HGP | 31 TCID$_{50}$ nonadsorbed | Day 4 Nontoxic at 108 mcg/ml Day 5 Toxic at 108–10.5 mcg/ml | | Active at 108–87 mcg/ml Inactive 108–10.5 mcg/ml |
| Example 4 | Tube | HeLa | Rhinovirus 2 HGP | 100 TCID$_{50}$ nonadsorbed | Day 4 Nontoxic at 100 mcg/ml Day 5 Toxic at 100–12.5 mcg/ml | | Active at 100 & 50 mcg/ml Inactive at 6.25 mcg/ml |
| | Disc | HeLa | Rhinovirus 2 HGP | 66 PFU/ml adsorbed | Day 5 Nontoxic (100 mcg disc) | | Inactive |
| Example 7 | Tube | HeLa | Rhinovirus 2 HGP | 20 TCID$_{50}$ nonadsorbed | Day 4 Nontoxic at 100 mcg/ml Day 5 V.Sl.Toxic at 100 mcg/ml | | Active at 100 & 50 mcg/ml Active at 100 & 50 mcg/ml |
| | Disc | HeLa | Rhinovirus 2 HGP | 970 PFU/ml adsorbed | Day 5 Nontoxic (100 mcg/disc) | | Inactive |

The compounds of Examples 4 and 13 showed antiviral activity after four days of incubation in the liquid test. An undetermined toxic effect on the cells was observed in the test system, however. The compound of Example 7 showed activity at two concentrations in the liquid system on both the 4th and 5th days of incubation, however a very slight toxic effect of undetermined origin was noted on day 5. The compounds of Examples 4 and 7 when tested by the solid media method showed the compounds to be inactive, thus suggesting that these compounds did not difuse through agar since they had shown activity in the liquid system.

We claim:

1. 3-Phenylhydroindoles of the formula:

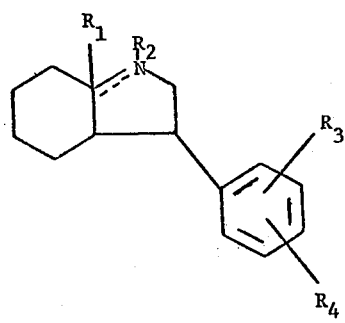

wherein $R_1$ may be hydrogen, lower alkyl, phenyl, or may be absent; $R_2$ may be hydrogen, hydroxy, lower alkyl or absent; or where $R_1$ is absent, $R_2$ may be $CH_3^+I^-$ or O; and $R_3$ and $R_4$ may be hydrogen, hydroxy or lower alkoxy.

2. A compound as set forth in claim 1 wherein $R_1$ is absent, $R_2$ is oxygen, $R_3$ is 3'-methoxy and $R_4$ is 4'-methoxy which is 3,3a,4,5,6,7-hexahydro-3-(3,4-dimethoxyphenyl)-2H-indole 1-oxide.

3. A compound as set forth in claim 1 wherein $R_1$ and $R_2$ are non-existent, $R_3$ is 3'-methoxy and $R_4$ is 4'-methoxy which is 3-(3,4-dimethoxyphenyl)-3,3a,4,5,6,7-hexahydro-2H-indole.

4. A compound as set forth in claim 1 wherein $R_1$ and $R_2$ are hydrogen, $R_3$ is 3'-methoxy and $R_4$ is 4'-methoxy which is 3-(3,4-dimethoxyphenyl)hexahydroindoline.

5. A compound as set forth in claim 1 wherein $R_1$ is absent, $R_2$ is $CH_3^+I^-$, $R_3$ is 3'-methoxy and $R_4$ is 4'-methoxy which is 3-(3,4-dimethoxyphenyl)-3,3a,4,5,6,7-hexahydro-1-methyl-2H-indolinium iodide.

6. A compound as set forth in claim 1 wherein $R_1$ is methyl, $R_2$ is hydrogen, $R_3$ is 3'-methoxy and $R_4$ and 4'-methoxy which is 3-(3,4-dimethoxyphenyl)hexahydro-7a-methylindoline.

7. A compound as set forth in claim 1 wherein $R_1$ and $R_2$ are methyl, $R_3$ is 3'-methoxy and $R_4$ is 4'-methoxy which is 3-(3,4-dimethoxyphenyl)hexahydro-1,7a-dimethylindoline.

8. A compound as set forth in claim 1 wherein $R_1$ is phenyl, $R_2$ is hydroxy, $R_3$ is 3'-methoxy and $R_4$ is 4'-methoxy which is 3-(3,4-dimethoxyphenyl)hexahydro-1-hydroxy-7a-phenylindoline.

9. A compound as set forth in claim 1 wherein $R_1$ is phenyl, $R_2$ is hydrogen, $R_3$ is 3'-methoxy and $R_4$ is 4'-methoxy which is 3-(3,4-dimethoxyphenyl)hexahydro-7a-phenylindoline.

10. A compound as set forth in claim 1 wherein $R_1$ is absent, $R_2$ is oxygen, $R_3$ and $R_4$ are hydrogen which is 3,3a,4,5,6,7-hexahydro-3-phenyl-2H-indole 1-oxide.

11. 3-(3,4-dimethoxyphenyl)hexahydro-1-hydroxyendoline.

12. 3-(3,4-dimethoxyphenyl)hexahydro-1-hydroxy-7a-methylindoline.

13. 3,3a,4,5,6,7-hexahydro-3-(2-methoxyphenyl)-2H-indole-1-oxide.

* * * * *